United States Patent [19]

Bozich

[11] Patent Number: 5,275,589
[45] Date of Patent: Jan. 4, 1994

[54] RUBBER BASED NON-PRESSURE SENSITIVE HOT MELT ADHESIVE AND APPLICATION

[75] Inventor: Frank Bozich, Franklin Park, Ill.

[73] Assignee: H. B. Fuller Company, Arden Hills, Minn.

[21] Appl. No.: 736,958

[22] Filed: Jul. 30, 1991

Related U.S. Application Data

[63] Continuation-in-part of Ser. No. 711,371, Jun. 3, 1991, which is a continuation of Ser. No. 518,102, May 1, 1990, abandoned, which is a continuation-in-part of Ser. No. 279,837, Dec. 5, 1988, abandoned.

[51] Int. Cl.$^5$ .................... C08K 5/01; C08L 91/08; A61F 13/15
[52] U.S. Cl. .................... 604/373; 604/358; 604/367; 524/487
[58] Field of Search ............... 530/214; 524/277, 487; 604/358, 365, 366, 367, 372, 373, 389

[56] References Cited

U.S. PATENT DOCUMENTS

| | | |
|---|---|---|
| 3,970,623 | 7/1976 | Feeney . |
| 4,136,071 | 1/1979 | Korpman . |
| 4,394,915 | 7/1983 | Nelson . |
| 4,419,494 | 12/1983 | Puletti . |
| 4,500,661 | 2/1985 | Lakshmanan ............ 524/487 |
| 4,526,577 | 7/1985 | Schmidt, Jr. et al. ........... 604/366 |
| 4,578,302 | 3/1986 | Schmidt . |
| 4,704,110 | 11/1987 | Raykovitz et al. ............ 604/366 |
| 5,057,571 | 10/1991 | Malcolm . |
| 5,093,406 | 3/1992 | Lossner . |
| 5,149,741 | 9/1992 | Alper et al. ............ 524/274 |

Primary Examiner—Randall L. Green
Assistant Examiner—A. Zuttarelli
Attorney, Agent, or Firm—Donald Pochopien

[57] ABSTRACT

The present invention is directed to a rubber based non-pressure sensitive hot melt adhesive composition and disposable diapers of the two or three ply type that are constructed using the adhesive. The rubber based non-pressure sensitive hot melt of the present invention comprises:

(A) from about 15% to about 39% of A-B-A or A-B-A-B-A-B multi-block copolymer wherein polymer blocks A are styrene blocks and polymer blocks B are butadiene blocks or hydrogenated butadiene blocks and wherein said polymer blocks A comprise from about 15 parts to about 60 parts per 100 parts polymer;

(b) from about 50% to about 75% by weight of one or more compatible tackifying resins having a composite Ring and Ball softening point from about 25° C. to about 50° C.;

(c) from about 2.5% to about 10% by weight of one or more waves; and (d) from about 0.1% to about 1.5% by weight of one or more antioxidant type stabilizers.

The adhesive of the present invention has no pressure sensitivity, an extremely long open time when applied to low temperatures and a very steep viscosity profile below the application temperature.

25 Claims, No Drawings

RUBBER BASED NON-PRESSURE SENSITIVE HOT MELT ADHESIVE AND APPLICATION

This application is a continuation-in-part of U.S. patent application Ser. No. 07/711,371, filed on Jun. 3, 1991, now pending, which is a continuation of U.S. Ser. No. 07/518,102, filed on May 1, 1990 and now abandoned, which is a continuation-in-part of U.S. Ser. No. 07/279,837 filed on Dec. 5, 1988 and now abandoned.

FIELD OF THE INVENTION

The present invention is directed to a rubber based non-pressure sensitive hot melt adhesive composition and to disposable diapers constructed using the adhesive. As properties, the adhesive of the present invention exhibits no pressure sensitivity at room temperature. It also has an extremely long open time when applied at low temperatures, a low initial viscosity at the application temperature and a very steep visocisty profile below the application temperature. These properties make the adhesive composition of the present invention particularly useful in the construction of disposable diapers of the two or three ply type.

B. Prior Art

Hot melt adhesive compositions are well known throughout the disposables industry. However, it is equal well known that a hot melt adhesive composition which is suited for bonding in one application, such as a two ply diaper, may be completely unsuitable for bonding in other applications, such as a three ply diaper.

The traditional two ply disposable diaper consists of an outer polyethylene or polypropylene film ("poly film"), an inner non-woven polyethylene or polypropylene film, preferably polypropylene, between which is a wood pulp filler, and a super absorbent material, with the layers being bonded together using a hot melt pressure sensitive adhesive. The traditional method of two ply construction and the hot melt pressure sensitive adhesives used therein described in U.S. Pat. No. 4,526,577 by Schmidt, et al. and is incorporated herein by reference. In the traditional method, a hot melt pressure sensitive adhesive is applied for example to a polypropylene film in a multi-line, multi-dot, or spray (collectively "multi-line") application, thus requiring that the adhesive have a high degree of adhesion. The wood pulp filler and super absorbent materials are then put down, and overlaid with a non-woven film that is "nipped" onto the outer polypropylene film to construct the diaper. In this method, the diameter's outside surface is the polypropylene film, which prevent moisture from escaping from the diaper onto the infants clothes, whereas the diaper's inside surface is the non-woven film (i.e., a porous polyethylene or polypropylene film) which allows moisture to penetrate and be retained by the absorbent that is held between the polypropylene and non-woven films. The above described two ply diaper has been used for about ten years. However, one drawback from the marketing perspective is that the polypropylene film on the outside gives the diaper a synthetic or plastic appearance and feel.

A new and very popular style of diaper has come onto the market which has addressed the synthetic feel or perception of the diaper. This new style diaper is of a similar construction to the aforementioned diaper but is made from three films (three ply) as opposed to the traditional tow films (two ply). In the these ply diaper, the additional ply or film is a non-woven polypropylene film that forms the outer surface of the diaper. This gives the exterior of the diaper a softer, less plastic and more aesthetically pleasing feel. The construction materials being used in the new type three ply diaper are similar to the materials used in the two ply diaper except that the poly film is a 0.5–0.55 mil blown polypropylene and the new outer surface is a 17.5 gm/sq. meter nonwoven film, such as a spun bonded polypropylene. In contrast, the traditional poly film used in the two ply diaper construction is a heavy gauge 1–1.5 mil cast embossed polypropylene film. The thinner (0.55 mil) films of the new style diaper constructions are mush less expensive than the heavier gauge films used in two ply diaper constructions. However, due to their decreased thickness, 0.5 mil films are much more susceptible to thermal distortion than the 1–1.5 mil films. Whereas the traditional diaper is constructed by applying the hot melt adhesive directly to the polypropylene film at about 275° F., the thinner polypropylene film of the new style construction requires that the hot melt adhesive be applied to the heavier, non-woven film in order to avoid entirely new set of problems for the adhesive presents an entirely new set of problems for the adhesive formulator.

There are several other problems inherent in the construction of the three ply diaper. In three ply construction, the outer nonwoven film and the polypropylene film are first combined to form a polypropylene/non-woven laminate. One problem in forming the laminate is that the outer non-woven is porous and a pressure sensitive adhesive can penetrate the pores of the non-woven film and cause the outside surface of the polypropylene/non-woven laminate to be sticky to the touch. Furthermore, since the polypropylene/nonwoven laminate is rerolled prior to combination with the absorbent and inner non-woven film, any penetration of adhesive through the outer non-woven will cause the adhesive to stick to the poly film under it on the rewound roll.

The adhesive used in three ply construction must possess sufficient adhesive and cohesive strength to provide high tensile strength bonds which are strong enough to survive in-line slitting operations. A bond strength of 100 gm. per linear inch peel is the industry standard. Presently the adhesive being used in the construction of the polypropylene/non-woven laminate of three ply diapers is a solvent born adhesive which is applied to the polypropylene film. A problem with the solvent-born adhesive it that it requires extended curing times thereby precluding the three ply diaper from being trimmed in-line. Typical of such solvent born adhesives is an adhesive produced by Shell Chemical Co. comprising: 100 parts Kraton D1111, an SIS rubber block copolymer 140 parts Escorex 1310, a tackifier (Exxon Chemicals); 10 parts Shell Flex 371, a plasticizing oil; 40 parts Piccovar A833, Hercules Chemical; and 2 parts of an antioxidant.

Additionally, any adhesive used in three ply construction must remain flexible and secure with age and not break down in a wet environment, such as a soiled diaper.

Typical adhesive used in 2 ply disposable diaper construction, which are unsuited for 3 ply construction for the previously stated reasons, are disclosed in U.S. Pat. Nos. 4,526,577 (Schmidt Jr. et al.) and 4,299,745 (Godfry). The Schmidt adhesive is a hot melt pressure sensitive adhesive comprising four classes of components: a block or multi-block copolymer; tackifying resins having high softening points (about 100°-120° C.); a plasticizing oil; optionally, a petroleum wax; and one or more stabilizers. The Godfrey adhesive comprises: polyethylene; ethylene vinylacetate; at least one tackifying resin; and a microcrystalline wax.

An object of the present invention is to provide an adhesive useful in the construction of two ply and/or three ply diapers which is not pressure sensitive, which has a steep temperature dependent viscosity profile, which eliminates the longer cure times necessary for the solvent born adhesives and the environmental and cost problems associated with using solvents, but which retains high tensile strength, remains flexible and secure with age and does not break down in a wet environment.

SUMMARY OF THE INVENTION

The present invention is directed to a rubber based non-pressure sensitive hot melt adhesive composition and disposable diapers constructed using the adhesive. The adhesive of the present invention has no pressure sensitivity at room temperature, has an extremely long open time when applied at low temperature, has low initial viscosity at the application temperature and a very steep viscosity profile below the application temperature. These properties make the adhesive composition of the present invention particularly useful in the construction of disposable diapers of the type using two or more polyethylene or polypropylene films.

The adhesive of the present invention comprises:

(a) from about 15% to about 39% by weight of an A-B-A or A-B-A-B-A-B multi-block copolymer wherein polymer blocks A are styrene blocks and polymer blocks B are butadiene blocks or hydrogenated butadiene blocks and wherein said polymer blocks A comprise about 15 parts to about 60 parts per 100 parts copolymer by weight.

(b) from about 50% to about 75% by weight of one or more compatible tackifying resins having a composite Ring and Ball softening point from about 25° C. and to about 50° C.;

(c) from about 2.5% to about 10% by weight of one or more waxes; and

)d from about 0.1% to about 1.5% by weight of one or more antioxidant type stabilizers.

The present invention is also directed to improved diapers of the 2 to 3 ply type employing the adhesive composition of the present invention.

DETAILED DESCRIPTION OF THE INVENTION

The present invention has multiple aspect including, a non-pressure sensitive hot melt adhesive composition, and a disposable diaper of the two ply or three ply type constructed using the adhesive of the present invention.

The adhesive composition of the present invention comprises:

(a) from about 15% to about 39% by weight of an A-B-A or A-B-A-b-A-B multi-block copolymer wherein polymer blocks A are styrene blocks and polymer blocks B are butadiene blocks or hydrogenated butadiene blocks and wherein said polymer blocks A comprise about 15 parts to about 60 parts per 100 parts copolymer by weight;

(b) from about 50% to about 75% by weight of one or more compatible tackifying resins having a composite Ring and Ball softening point from about 25° C. to about 50° C.;

(c) from about 2.5% to about 10% by weight of one or more waxes; and (d) from about 0.1% to about 1.5% by weight of one or more antioxidant type stabilizers.

The A-B-A or A-B-A-B-A-B multi-block copolymer of the present invention employ polystyrene as the "A"0 block and butadiene or hydrogenated butadiene as the "B" block. The copolymer may be prepared using the methods taught (for example,) in U.S. Pat. Nos. 3,239,478; 3,427,269 and 3,932,327 which are incorporated herein by reference. Alternatively, many of these copolymers are commercially available from Enichem America, (New York, New York), under the tradenames Solt 168 and Solt 166 or from Shell (Oil) Chemical Company under the tradenames Kraton 1101, 1102, 1656, 1652 and 1657.

A most preferred copolymer for use in the present invention is the copolymer Solt 168, wherein the A block is polystyrene and the B block is butadiene and which are present in the relative amounts of 45% styrene and 57% butadiene by weight. In a preferred embodiment of the present invention, the copolymer comprises from about 15% by weight to about 28% by weight of the adhesive composition. In a most preferred embodiment of the present invention, the copolymer comprises about 19% by weight of the adhesive composition.

The tackifying resin component of the present invention comprises one or more tackifying resins with a composite Ring and Ball softening point of from about 25° C. to about 50° C. By "composite Ring and Ball softening point" as used herein in relation to the tackifying resins is meant either the Ring and Ball softening point of the individual tackifier when only a single tackifier makes up the tackifying resin component or the Ring and Ball softening point of the tackifier blend when more than one tackifier makes up the tackifying resin component. A preferred tackifying resin component includes a blend of three tackifying resins comprising from about 45 parts to about 65 parts (by weight per 100 parts tackifying resin component) of a (first) tackifying resin having Ring and Ball softening point from about 100° C. to about 110° C.; from about 13 parts to about 26 parts of a (second) tackifying resin having a Ring and Ball softening point of about 20° C.; and from about 20 parts to about 27 parts of a (third) tackifying resin having a Ring and Ball softening point of about 10° C. Most preferred is a blend of tackifying resins comprising about 63 parts of a light colored hydrocarbon resin tackifier with a Ring and Ball Softening point of about 100° C. to 110° C., an example of which is commercially available under the tradename Escorez 149-A from Exxon Chemicals, (Baton Rouge, La.); about 13 parts of a synthetic petroleum hydrocarbon resin having an Ring and Ball softening point of about 20° C., an example of which is commercially available under the tradename Escorez 2520 from Exxon Chemicals; and about 24 parts of a synthetic polyterpene resin tackifier having a Ring and Ball softening point of about 10° C., an example of which is commercially available as Wingtack 10 from Goodyear Chemical Co., (Akron, Ohio).

It is also within the scope of the invention to employ a single tackifying resin as the tackifying resin component of the invention. As with the mixture of tackifiers, the single tackifying resin should be compatible with the other ingredients and itself have a ring and Ball softening point of between about 25° C. and about 50° C.

The tackifying mixture of the preferred embodiment of the present invention comprises from about 69% to about 73% by weight of the adhesive composition.

The wax component of the present invention comprises from about 2.5% to about 10% of one or more waxes. Preferred waxes include but are not limited to paraffin waxes, microcrystalline waxes, and synthetic waxes. Preferred in the present invention is a mixture of waxes comprising from about 5.5% to about 6.5% by weight (relative to the weight of the adhesive composition) of a paraffin wax and from about 2.5% to about 4.1% by weight of a synthetic wax. A most preferred combination of waxes comprises about 3.9% by weight of a petroleum wax and about 5.7% by weight of a synthetic wax. Preferred petroleum waxes have a melting point of about 147° F., an oil content of about 0.3%, a needle penetration value of from about 12 to about 13 at 77° F. and from about 26 to about 50° at 100° F., and a viscosity of about 41 centipoise at 210° F. Preferred petroleum waxes are exemplified by but not limited to commercially available waxes such as 6973 from National Wax Co., (Skokie, Ill.). Preferred synthetic waxes have a Brookfield viscosity of about 27 centipoise at 121° C., a Ring and Ball Softening point from about 112° C. to about 115° C., needle penetration values (1/10 millimeter) of about 2.5 to about 3 at 25° C., and about 6° to 60° C., and a density of about 0.95 g/ml at 25° C. Preferred synthetic waxes are exemplified by but not limited to commercially available waxes such as Escomer H101 available from Exxon Chemicals.

The adhesive composition of the present invention also comprises from 0.1% to about 1.5% by weight of one or more stabilizers. Preferred stabilizes are of the antioxidant type. Generally, these antioxidants are either high molecular weight sterically hindered phenols or sulfur or phosphorous substituted phenols. By the term "sterically hindered phenols" is generally meant those phenols with either two isopropyl or preferably two tertiary butyl groups ortho to the phenolic hydroxyl group. Representative "sterically hindered phenols" include, but are not limited to, 1,3,5-trimethyl-2,2,6-tris(3,5-di-tert-butyl-4-hydroxybenzyl)benzene; pentaerythritol tetrakis-3(3,5-di-tert-butyl-4-hydroxyphenyl)-propionate; n-octadecyl-3-(3,5-di-tert-butyl-4-hydroxyphenyl)-propionate; 4,4'-methylenebis(2,6-tert-butylphenol); 4,4'-thiobis(6-tert-butyl-o-cresol); 2,6-di-tert-butylphenol; 6-(4-hydroxyphenoxy)-2,4-bis(n-octylthio)-1,3,5-triazine; di-n-octadecyl 3,5-di-tert-butyl-4-hydroxybenzylphosphonate; 2-(n-octylthio)ethyl 3,5-di-tert-butyl-4-hydroxybenzoate; and sorbitol hexa[3-(3,5-di-tert-butyl-4hydroxyphenyl)propionate].

A most preferred antioxidant is pentaerythritol tetrakis-3(3,5-di-tert-butyl-4-hydroxyphenyl)propionate which is commercially available as Irganox 1010 from Ciba-Geigy, (Hawthorne, N.Y.). However, any other compatible antioxidant or combination of antioxidants may be used without departing from the scope of the invention.

The ideal adhesive properties for use in disposable diaper construction include a lack of pressure sensitivity at room temperature, that it have an extremely long open-time to enable it to bond to the polypropylene sheet after it has been applied at around 225° C. on the non-woven, a very low initial viscosity allowing it to be applied at temperatures around 225° F., a very steep viscosity profile below the application temperature so that it reaches a viscosity of over 1 million centipoises over a very short temperature drop, and a bond strength between the non-woven films and polypropylene of over 100 gm./inch.

We have tested out hot melt adhesive composition for this application and have found that it meets all of the above requirements. The samples tested are indicated below as Sample #'s 1, 2, & 3. In this group, Sample #1 is an example of a prior art type pressure sensitive adhesive which is included for comparative purposes to demonstrate the advantages of non-pressure sensitive adhesives in diaper construction. Sample #2 represents a preferred embodiment of the present invention and Sample #3 represents the most preferred embodiment of the present invention.

|  | wt. % |
|---|---|
| Sample #1 | |
| SOLT 168 | 20.0 |
| Wingtack 10 | 25.4 |
| Escorez 149-A | 30.0 |
| Escorez 2520 | 24.0 |
| Irganox 1010 | 0.6 |
|  | 100.0 |
| Sample #2 | |
| SOLT 168 | 19.0 |
| WING-TACK 10 | 18.0 |
| Escorez 149-A | 34.8 |
| Escorez 2520 | 19.0 |
| Irganox 1010 | 0.4 |
| Escomer H101 | 6.0 |
| 6973 | 2.8 |
|  | 100.0 |
| Sample #3 | |
| SOLT 168 | 19.0 |
| Wingtack 10 | 17.1 |
| Escorez 149-A | 44.4 |
| Escorez 2520 | 9.5 |
| Irganox 1010 | 0.4 |
| Escomer H101 | 5.7 |
| 6973 | 3.9 |
|  | 100.0 |

For the purposes of comparison a pressure sensitive hot melt adhesive (Sample #1) was compared to a preferred embodiment of the present invention (Sample #2) and the most preferred embodiment of the present invention (Sample #3) for their viscosity profiles as a function of temperature, their heat resistance, and for their blocking characteristics. "Blocking" refers to the tendency of an adhesive to penetrate through the non-woven film thus causing the polypropylene/non-woven laminates to stick together when rerolled.

The temperature dependence of viscosity for Samples #1, #2 and #3 were measured using a Brookfield Viscometer and the results are shown in Table I.

TABLE I

Viscosity Profiles

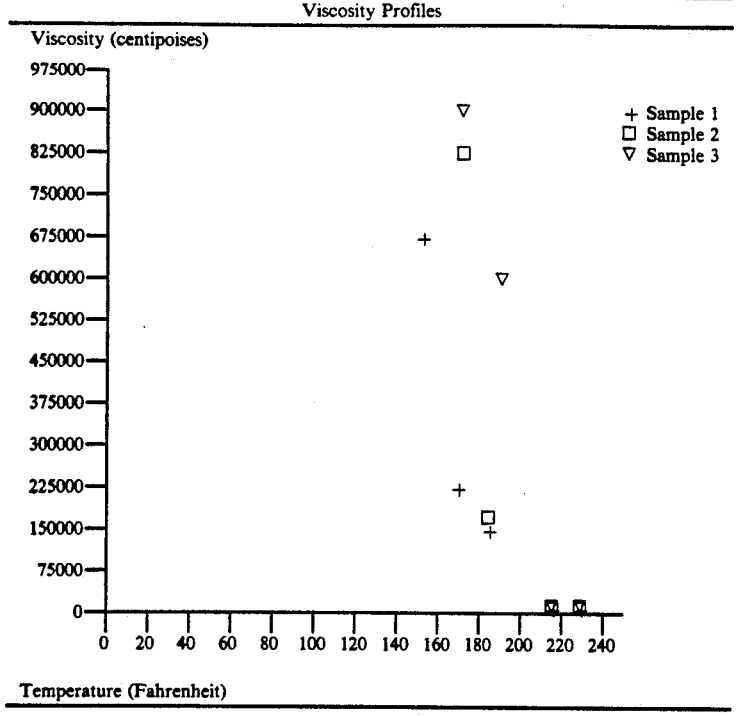

Temperature (Fahrenheit)

As can be seen in Table I, the viscosity of all 3 Samples were similar at 225° F. However, the viscosity of Sample #1 increased to only about 662,500 cps at 150° F. (75° F. below the application temperature) while the viscosity of Sample #2 increased to about 820,000 cps at 165° C. (60° F. below the application temperature). The viscosity of Sample #3 increased to about 895,000 cps at 165° F. (60° F. below the application temperature). These results show that the Sample #2 (the preferred embodiment, and Sample #3 (the most preferred embodiment) have steep temperature versus viscosity profiles which prevents the adhesive from penetrating the non-woven layer at temperatures below the application temperature of 225° F.

In order to examine the blocking characteristics of the adhesives, Sample #1, #2 and #3 were used to construct polypropylene/non-woven laminates. The adhesives were applied at 225° F. and the polypropylene/non-woven laminates were wound into a roll. Upon unwinding, the polypropylene/non-woven laminates made with Sample #2 or #3 exhibited no blocking because the adhesives did not penetrate the non-woven sheet of the laminate due to their steep temperature versus viscosity profiles. However, when the adhesive of Sample #1 was used to prepare the polypropylene/non-woven laminate it caused blocking on the rewound roll, due to the fact that it penetrated the non-woven layer of laminate. In fact, the tacking was sufficient to distort the poly film when the polypropylene/non-woven laminate was unrolled. This was due to Sample #1 being pressure sensitive and also having a relatively flat viscosity profile (when compared to the adhesives of the present invention) causing it to penetrate the non-woven layer at temperatures significantly below the application temperature.

The bond strengths of Sample #1, #2 and #3 were tested by applying the adhesives during construction of the polypropylene/non-woven laminate using a Graco/LTI Microprint rotary screen printer using a 60 mesh screen. Attempts were then made to manually pull the laminate apart. In each case the adhesive bond remained intact while the polypropylene and non-woven films were destroyed.

Laminates bonded with Samples #2 and #3 were heat tested in an oven for 24 hrs at 140° F. The laminates were subjected to 1 psi of pressure. The laminates were cut into strips 2 inches × 1 inch and stacked 2 plys high. They were stacked both non-woven to poly and non-woven to non-woven. Laminates made with Sample #3 showed no tacking after 24 hrs., whereas material stacked poly to non-woven with Sample #2 exhibited a very slight tack.

The non-pressure sensitive rubber-based hot melt adhesive of the present invention offers several advantages over both the traditional hot melt pressure sensitive adhesives and the solvent-born adhesives presently in use. These advantages are in the area of superior adhesion, in speed of set, in the lack of pressure sensitivity and in the extremely steep temperature dependent viscosity profile.

Because the hot melt adhesive composition of the present invention binds poly to non-woven but without penetration of the porous non-woven, it is suitable for the production of both the 2 ply and the 3 ply disposable diapers. Thus, another aspect of the present invention is an improved disposable diaper of the 2 ply or 3 ply type, which is constructed as described above. Specifically, the present invention is directed to a disposable diaper of the 2 ply type comprising an outer poly film (moisture barrier), preferably polypropylene, an inner non-woven (porous) film, typically a porous polypropylene non-woven film, a filler and an absorbent positioned between the outer poly and inner non-woven films, and an adhesive for adhering the poly film to the non-woven film and for fixing the filler and absorbent therebetween, the adhesive comprising a rubber based non-pressure sensitive adhesive comprising:

(a) from about 15% to about 39% by weight of the A-B-A-B-A-B multi-block copolymer wherein polymer blocks A are styrene blocks and polymer blocks B are butadiene blocks or hydrogenated butadiene and wherein said polymer block A comprises about 15 parts to about 60 parts per 100 parts copolymer by weight;

(b) from about 50% to about 75% by weight of one or more compatible tackifying resins having a composite Ring and Ball softening point from about 25° C. to about 50° C.;

(c) from about 2.5% to about 10% by weight of one or more waxes; and (d) from about 0.1% to about 1.5% by weight of one or more antioxidant type stabilizers.

The present invention also includes the disposable diaper described above further containing a porous outer film, preferably a non-woven film, that has been affixed to the outer poly film by the described adhesive composition of the present invention. The resultant diaper is the 3 ply type. In a preferred embodiment of the 2 or 3 ply disposable diaper of the present invention the adhesive comprises:

(a) from about 17% to about 21% by weight of an A-B-A or A-B-A-B-A-B multi-block copolymer wherein polymer blocks A are styrene blocks and polymer blocks B are butadiene or hydrogenated butadiene blocks and wherein said polymer blocks A comprises from about 5 parts to about 40 parts per 100 parts copolymer by weight;

(b) from about 69% to about 73% by weight of one or more compatible tackifying resins having a composite Ring and Ball softening point from about 25° C. to about 50° C.;

(c) from about 7.5% to about 10% by weight of one or more waxes; and (d) from about 0.2% to about 1.0% by weight of one or more antioxidant type stabilizers.

In a most preferred embodiment of the 2 or 3 ply disposable diaper of the present invention, the adhesive comprises:

(a) about 19% by weight of an A-B-A or A-B-A-B-A-B multi-block copolymer wherein polymer blocks A are styrene blocks and polymer blocks B are butadiene blocks or hydrogenated butadiene and wherein said polymer block A comprises about 43 parts per 100 parts polymer and wherein said polymer block B comprises 57 parts per 100 parts copolymer by weight:

(b) about 71% by weight of a mixture of three tackifying resins comprising about 63 parts of a light colored hydrocarbon resin having a Ring and Ball softening point of about 100°-110° C.; about 13 parts of a synthetic petroleum hydrocarbon resin having a Ring and Ball softening point of about 20° C.; and about 24 parts of a synthetic polyterpene resin having a Ring and Ball softening point of around 10° C.;

(c) about 5.7% by weight by weight of a synthetic wax and about 3.9% by weight of a petroleum wax; and (d) about 0.4% by weight of a sterically hindered phenolic antioxidant.

In a preferred embodiment of the 2 ply or 3 ply disposable diaper of the present invention, the poly film is replaced by a moisture impermeable, vapor permeable film. Such a film is the polytetrafluoroethylene film that is commercially available under the tradename Goretex ®.

DESCRIPTION OF THE PREFERRED EMBODIMENT

The rubber based hot melt adhesive of Sample #2 and #3 were prepared by adding Wingtack 10 to a kettle preheated to 325° F. followed by the addition of Irganox 1010 and then by the addition of Escorex 149-A. When the Escorez 149-A was melted and when the mixture in the kettle was smooth, Soft 168 was added and the mixture was again mixed until smooth, followed by the addition of Escorex 2520. The mixture was then mixed for 30 minutes before adding Escomer H101, followed by 6973. Finally, the mixture was mixed until smooth.

What is claimed is:

1. A rubber based non-pressure sensitive hot melt adhesive composition comprising:

(a) from about 15% to about 39% of said composition by weight of an A-B-A or A-B-A-B-A-B multi-block copolymer, wherein polymer blocks A are styrene blocks and polymer blocks B are butadiene blocks or hydrogenated butadiene blocks and wherein said polymer blocks A comprise from about 15 parts to about 60 parts per 100 parts of said copolymer by weight;

(b) from about 50% to about 75% of said composition by weight of one or more compatible tackifying resins having a composite Ring and Ball softening point from about 25° C. to about 50° C.;

(c) from about 2.5% to about 10% of said composition by weight of one or more waxes; and (d) from about 01.% to about 1.5% of said composition by weight of one or more antioxidant type stabilizers, said adhesive composition being characterized by being non-pressure sensitive at room temperature, by having a steep temperature dependent viscosity profile, and by being substantially oilless.

2. The adhesive composition of claim 1 wherein said copolymer is an A-B-A-B-A-B multi-block copolymer.

3. The adhesive composition of claim 2 wherein said multi-block copolymer consists essentially of from about 43 parts to about 57 parts styrene per 100 parts copolymer by weight and from about 57 parts to about 43 parts butadiene or hydrogenated butadiene per 100 parts copolymer by weight.

4. The adhesive composition of claim 3 wherein said one or more compatible tackifying resins comprises a blend of (1) a light colored hydrocarbon resin having a Ring and Ball softening point of from about 100° C. to about 110° C., (2) a synthetic petroleum hydrocarbon resin having a Ring and Ball softening point of about 20° C. and (3) a synthetic polyterpene resin tackifier having a Ring and Ball Softening point of about 10° C.

5. The adhesive composition of claim 4 containing a first wax and a second wax.

6. The adhesive composition of claim 5 wherein said first and said second waxes are chosen from the group consisting of paraffin waxes, synthetic waxes and mixtures thereof.

7. The adhesive composition of claim 6 wherein said one or more stabilizers is one or more sterically hindered phenolic antioxidants.

8. The adhesive composition of claim 1 comprising:

(a) from about 17% to about 21% of said composition by weight of an A-B-A or A-B-A-B-A-B multi-block copolymer wherein polymer blocks A are styrene blocks and polymer blocks B are butadiene or hydrogenated butadiene blocks and wherein said polymer blocks A comprise from about 15 parts to about 60 parts per 100 parts of said copolymer by weight;

(b) from about 69% to a about 73% of said composition by weight of one or more compatible tackifying resins having a composite Ring and Ball softening point from about 25° C. to about 50° C.;

(c) from about 7.5% to about 10% of said composition by weight of one or more waxes; and (d) from about 0.2% to about 1.0% of said composition by weight of one or more antioxidant type stabilizers.

9. A rubber based non-pressure sensitive adhesive composition comprising:

(a) about 19% of said composition by weight of an A-B-A or A-B-A-B-A-B multi-block copolymer wherein polymer blocks A are styrene blocks and polymer blocks B are butadiene blocks or hydrogenated butadiene and wherein said polymer blocks A comprise about 43 parts per 100 parts of said copolymer by weight and wherein said polymer blocks B comprise about 57 parts per 100 parts of said copolymer by weight;

(b) about 71% of said composition by weight of a mixture of three tackifying resins comprising about 63 parts per 100 parts of said resin mixture by weight of a light colored hydrocarbon resin having a Ring and Ball softening point of about 100°–110° C.; about 13 parts per 100 parts of said resin mixture by weight of a synthetic petroleum hydrocarbon resin having a Ring and Ball softening point of about 20° C.; and about 24 parts per 100 parts of said resin mixture by weight of a synthetic polyterpene resin having a Ring and Ball softening point of about 10° C., said resin mixture having a composite Ring and Ball softening point from about 25° C. to about 50° C.;

(c) about 5.7% of said composition by weight of a synthetic wax and about 3.9% by weight of a paraffin wax; and (d) about 0.4% of said composition by weight of a sterically hindered phenolic antioxidant, said adhesive composition being characterized by being non-pressure sensitive at room temperature, by having a steep temperature dependent viscosity profile, and by being substantially oilless.

10. A composition of matter comprising in combination the adhesive composition of claim 1 and a poly film.

11. The composition of claim 10 further including a non-woven film.

12. The composition of claim 11 further including in combination an absorbent for moisture between said poly film and said non-woven film.

13. A disposable two ply diaper, comprising an outer poly film, an inner non-woven film, a filler and an absorbent positioned between the outer poly film and the inner non-woven film, and a rubber based non-pressure sensitive adhesive composition for adhering said poly film to said non-woven film and for fixing said filler and absorbent therebetween, said rubber based non-pressure sensitive adhesive composition comprising:

(a) from about 15% to about 39% of said composition by weight of an A-B-A or A-B-A-B-A-B multiblock copolymer wherein polymer blocks A are styrene blocks and polymer blocks B are butadiene blocks or hydrogenated butadiene and wherein said polymer blocks A comprise about 15 parts to about 60 parts per 100 parts of said copolymer by weight;

(b) from about 50% to about 75% of said composition by weight of one or more compatible tackifying resins having a composite Ring and Bell softening point from about 25° C. to about 50° C.;

(c) from about 2.5% to about 10% of said composition by weight of one or more waxes; and pl (d) from about 01.% to about 1.5% of said composition by weight of one or more stabilizers said adhesive being characterized by having a steep temperature dependent viscosity profile and by being substantially oilless.

14. A disposable three ply diaper comprising an outer poly film, an inner non-woven film, a filler and an absorbent positioned between the outer poly film and the inner non-woven film, a porous non-woven poly film positioned over said outer poly film, and a rubber based non-pressure sensitive adhesive composition for adhering said poly film to said inner non-woven film, for fixing said filler and absorbent therebetween, and for adhering said porous non-woven poly film to said outer poly film, said rubber based non-pressure sensitive adhesive composition comprising:

(a) from about 15% to about 39% of said composition by weight of an A-B-A or A-B-A-B-A-B multiblock copolymer wherein polymer blocks A are styrene blocks and polymer blocks B are butadiene or hydrogenated butadiene blocks and wherein said polymer blocks A comprise from about 15 parts to about 60 parts per 100 parts of said copolymer by weight;

(b) from about 50% to about 75% of said composition by weight of one or more compatible tackifying resins having a composite Ring and Ball softening point from about 25° C. to about 50° C.;

(c) from about 2.5% to about 10% of said composition by weight of one or more waxes; and (d) from about 0.1% to about 1.5% of said composition by weight of one or more antioxidant type stabilizers said adhesive being characterized by having a steep temperature dependent viscosity profile and by being substantially oilless.

15. The disposable diaper of claim 14 wherein said copolymer is an A-B-A-B-A-B multiblock copolymer.

16. The disposable diaper of claim 15 wherein said multi-block copolymer consists essentially of from about 43 parts to about 57 parts styrene per 100 parts copolymer by weight, and from about 57 parts to about 43 parts butadiene or hydrogenated butadiene per 100 parts copolymer by weight.

17. The disposable diaper of claim 16 wherein said one or more compatible tackifying resins is a mixture of three compatible resins taken from the group consisting of (1) a light colored hydrocarbon resin having a Ring and Ball Softening point from about 100° C. to about 110° C., (2) a synthetic petroleum hydrocarbon resin having a Ring and Ball softening point of about 20° C. and (3) a synthetic polyterpene resin tackifier having a Ring and Ball Softening point of about 10° C.

18. The disposable diaper of claim 17 wherein said one or more waxes comprises a first and a second wax.

19. The disposable diaper of claim 18 wherein said first and said second waxes are chosen from the group consisting of paraffin waxes, synthetic waxes and mixtures thereof.

20. The disposable diaper of claim 19 wherein said one or more stabilizers is a sterically hindered phenolic antioxidant.

21. A disposable three ply diaper comprising an outer poly film, an inner non-woven film, a filler and an absorbent positioned between the outer poly film and the inner non-woven film, a porous non-woven poly film positioned over said outer poly film, and a rubber based non-pressure sensitive adhesive composition for adhering said poly film to said inner non-woven film, for fixing said filler and absorbent therebetween, and for adhering said porous non-woven poly film to said outer poly film, said rubber based non-pressure sensitive adhesive composition comprising:
(a) from about 17% to about 21% of said composition by weight of an A-B-A or A-B-A-B-A-B multi-block copolymer wherein polymer blocks A are styrene blocks and polymer blocks B are butadiene or hydrogenated butadiene blocks and wherein said polymer blocks A comprise from about 5 parts to about 40 parts per 100 parts of said copolymer by weight;
(b) from about 69% to about 73% of said composition by weight of one or more compatible tackifying resins having a composite Ring and Ball softening point from about 25° C. to about 50° C.;
(c) from about 7.5% to about 10% of said composition by weight of one or more waxes; and
(d) from about 0.2% to about 1.0% of said composition by weight of one or more antioxidant type stabilizers,
said composition being characterized by being non-pressure sensitive at room temperature, by having a steep temperature dependent viscosity profile, and by being substantially oilless.

22. A three ply disposable diaper comprising an outer poly film, an inner non-woven film, a filler and an absorbent positioned between the outer poly film and the inner non-woven film, a porous non-woven poly film positioned over said outer poly film, and a rubber based non-pressure sensitive adhesive composition for adhering said poly film to said inner non-woven film, for fixing said filler and absorbent therebetween, and for adhering said porous non-woven poly film to said outer poly film, said rubber based non-pressure sensitive adhesive composition comprising:
(a) about 19% of said composition by weight of an A-B-A or A-B-A-B-A-B multi-block polymer wherein polymer blocks A are styrene blocks and polymer blocks B are butadiene blocks or hydrogenated butadiene blocks and wherein said polymer blocks A comprise about 43 parts per 100 parts of said copolymer by weight and wherein said polymer blocks B comprise about 57 parts per 100 parts of said copolymer by weight;
(b) about 71% of said composition by weight of a mixture of three tackifying resins; said mixture comprising about 63 parts per 100 parts of mixture by weight of a light colored hydrocarbon resin having a Ring and Ball softening point of about 100° to about 110° C., about 13 parts per 100 parts of mixture by weight of a synthetic petroleum hydrocarbon resin having a Ring and Ball softening point of about 20° C., and about 24 parts per 100 parts of mixture by weight of a synthetic polyterpene resin having a Ring and Ball softening point of about 10° C., said resin mixture having a composite Ring and Ball softening point from about 25° C. to about 50° C.
(c) about 5.7% of said composition by weight of a synthetic wax and about 3.9% by weight of a paraffin wax; and
(d) about 0.4% of said composition by weight of a sterically hindered phenolic antioxidant,
said composition being characterized by being non-pressure sensitive at room temperature, by having a steep temperature dependent viscosity profile, and by being substantially oilless.

23. In a disposable three ply diaper comprising an outer poly film, an inner non-woven film, a filler and an absorbent positioned between the outer poly film and the inner non-woven film, a porous non-woven poly film positioned over said outer poly film, and an adhesive composition for adhering said poly film to said inner non-woven film, for fixing said filler and absorbent therebetween, and for adhering said porous non-woven poly film to said outer poly film, the improvement being said adhesive composition comprising:
(a) from about 15% to about 39% of said adhesive composition by weight of an A-B-A or A-B-A-B-A-B multi-block copolymer wherein polymer blocks A are styrene blocks and polymer blocks B are butadiene blocks or hydrogenated butadiene blocks and wherein said polymer blocks comprise from about 15 parts to about 60 parts per 100 parts of said copolymer by weight;
(b) from about 50% to about 75% of said adhesive composition by weight of one or more compatible tackifying resins having a composite Ring and Ball softening point from about 25° C. to about 50° C.;
(c) from about 1.5% to about 10% of said adhesive composition by weight of one or more waxes; and
(d) from about 0.1% to about 1.5% of said adhesive composition by weight of an antioxidant type stabilizer,
said adhesive composition being characterized by being non-pressure sensitive at room temperature, by having a steep temperature dependent viscosity profile, and by being substantially oilless.

24. In a disposable three ply diaper comprising an outer poly film, an inner non-woven film, a filler and an absorbent positioned between the outer poly film and the inner non-woven film, a porous non-woven poly film positioned over said outer poly film, and an adhesive composition for adhering said poly film to said inner non-woven film, for fixing said filler and absorbent therebetween, and for adhering said porous non-woven poly film to said outer poly film, the improvement being the adhesive composition comprising:
(a) from about 17% to about 21% of said adhesive composition by weight of an A-B-A or A-B-A-B-A-B multi-block copolymer wherein polymer blocks A are styrene blocks and polymer blocks B are butadiene or hydrogenated butadiene blocks and wherein said polymer blocks A comprise from about 15 parts to about 60 parts per 100 parts of said copolymer by weight;
(b) from about 69% to about 73% of said adhesive composition by weight of one or more compatible tackifying resins having a composite Ring and Ball softening point from about 25° C. to about 50° C.;
(c) from about 7.5% to about 10% of said adhesive composition by weight of one or more waxes; and (d) from about 0.2% to about 1.0% of said adhesive composition by weight of one or more antioxidant type stabilizers, said adhesive composition being characterized by being non-pressure sensitive at room temperature, by having a steep temperature dependent viscosity profile, and by being substantially oilless.

25. In a three ply disposable diaper, comprising an outer poly film, an inner non-woven film, a filler and an absorbent positioned between the outer poly and inner non-woven films, a porous non-woven poly film positioned over said outer poly film, and an adhesive composition for adhering said poly film to said inner non-woven film, for fixing said filler and absorbent therebetween, and for adhering said porous non-woven poly film to said outer poly film, the improvement being the adhesive composition comprising:

(a) about 19% of said adhesive composition by weight of an A-B-A or A-B-A-B-A-B multi-block copolymer wherein polymer blocks A are styrene blocks and polymer blocks B are butadiene or hydrogenated butadiene blocks and wherein said polymer blocks A comprise about 43 parts per 100 parts of said copolymer by weight and wherein said polymer blocks B comprise about 57 parts per 100 parts of said copolymer by weight;

(b) about 71% of said adhesive composition by weight of a mixture of three tackifying resins comprising about 63 parts per 100 parts resin mixture by weight of a light colored hydrocarbon resin having a Ring and Ball softening point of about 100° to about 110° C.; about 13 parts per 100 parts resin mixture by weight of a synthetic petroleum hydrocarbon resin having a Ring and Ball softening point of about 20° C.; and about 24 parts per 100 parts resin mixture by weight of synthetic polyterpene resin having a Ring and Ball softening point of about 10° C., said resin mixture having a composite Ring and Ball softening point from about 20° C. to about 50° C.;

(c) about 5.7% of said adhesive composition by weight of a synthetic wax and 3.9% by weight of a paraffin wax; and (d) about 0.4% of said adhesive composition by weight of a sterically hindered phenolic antioxidant, said adhesive composition being characterized by being non-pressure sensitive at room temperature, by having a steep temperature dependent viscosity profile, and by being substantially oilless.

* * * * *